United States Patent [19]

Bither, Jr.

[11] Patent Number: 4,632,916
[45] Date of Patent: Dec. 30, 1986

[54] FUMED SILICA MODIFIED CATALYST

[75] Inventor: Tom A. Bither, Jr., Wilmington, Del.

[73] Assignee: E. I. Du Pont de Nemours and Company, Wilmington, Del.

[21] Appl. No.: 754,752

[22] Filed: Jul. 15, 1985

[51] Int. Cl.$^4$ .................. B01J 27/198; B01J 27/182
[52] U.S. Cl. .................................. 502/209; 502/214
[58] Field of Search ............................ 502/209, 214

[56] References Cited

U.S. PATENT DOCUMENTS

| | | | |
|---|---|---|---|
| 3,625,863 | 12/1969 | Heller | 502/209 |
| 3,864,280 | 2/1975 | Schneider | 252/435 |
| 3,864,284 | 2/1975 | Schneider | 502/209 |
| 4,062,873 | 12/1977 | Harrison | 260/346.75 |
| 4,064,070 | 12/1977 | Harrison | 252/435 |
| 4,092,269 | 5/1978 | Mount et al. | 252/435 |
| 4,092,332 | 5/1978 | Freerler et al. | 502/209 X |
| 4,111,963 | 9/1978 | Mount et al. | 260/346.75 |
| 4,132,670 | 1/1979 | Katsumoto et al. | 252/437 |
| 4,147,661 | 4/1979 | Higgins et al. | 252/435 |
| 4,179,404 | 12/1979 | Borone | 502/209 |
| 4,187,235 | 2/1980 | Katsumoto et al. | 260/346.75 |
| 4,222,945 | 9/1980 | Higgins et al. | 260/346.75 |
| 4,333,853 | 6/1982 | Milberger et al. | 502/209 |
| 4,359,405 | 11/1982 | Mount et al. | 502/209 |
| 4,371,702 | 2/1983 | Bither | 549/260 |
| 4,386,215 | 5/1983 | Mount et al. | 502/209 X |
| 4,396,535 | 8/1983 | Bremer et al. | 502/209 X |
| 4,410,752 | 10/1983 | Blum et al. | 502/209 X |
| 4,434,244 | 2/1984 | Kuhlmann | 502/209 |
| 4,435,521 | 3/1984 | Yang et al. | 502/209 |
| 4,442,226 | 4/1984 | Bither | 502/209 |
| 4,481,304 | 11/1984 | Sato et al. | 502/214 X |
| 4,496,663 | 1/1985 | Hanson et al. | 502/209 |
| 4,510,259 | 4/1985 | Udovich et al. | 502/209 |
| 4,515,904 | 5/1985 | Edwards | 502/209 |
| 4,520,127 | 5/1985 | Otake et al. | 502/214 X |
| 4,525,471 | 6/1985 | Bremer et al. | 502/209 |

OTHER PUBLICATIONS

Published application U.S. Ser. No. B330,354, Mount et al.

*Primary Examiner*—Andrew H. Metz
*Assistant Examiner*—William G. Wright

[57] ABSTRACT

An improved vanadium/phosphorus catalyst for the oxidation of n-butane to maleic anhydride is disclosed. Preferably, the catalyst contains a promoter. A process for the oxidation of n-butane to maleic anhydride using the improved catalyst is also disclosed.

14 Claims, No Drawings

FUMED SILICA MODIFIED CATALYST

FIELD OF THE INVENTION

This invention relates to an improved vanadium/phosphorus oxide catayst for the oxidation of n-butane to maleic anhydride.

BACKGROUND OF THE INVENTION

Maleic anhydride is a commercially-important compound used in the manufacture of alkyd and polyester resins. It is also a versatile intermediate for chemical synthesis. n-butane is a relatively inexpensive feed used in the industrial production of maleic anhydride. Improved processes and catalysts for the oxidation of n-butane to maleic anhydride are of interest to the chemical industry.

Mount et al., published application U.S. Ser. No. B330,354 and U.S. Pat. No. 4,111,963, disclose a phosphorus/vanadium/oxygen catalyst and a method of preparing dicarboxylic acid anhydrides by contacting the catalyst with saturated hydrocarbons. More specifically, the Patentees disclose the preparation of maleic anhydride using a phosphorus/vanadium/oxygen catalyst. Oxygen-containing vanadium and phosphorus compounds are contacted to form a catalyst precursor. The importance of reducing the vanadium to valence +4 is described. The precursor is shaped and calcined to form a catalyst. The preferred catalyst has a P/V atom ratio of about 1:2 to 2:1 and a porosity of at least about 35%. The catalyst is contacted with saturated hydrocarbons at a temperature from about 350° to 600° C. to form maleic anhydride.

U.S. Pat. No. 3,864,280 issued to Schneider, discloses the preparation of a phosphorus/vanadium mixed oxide catalyst composition for the oxidation of hydrocarbons. The catalyst is prepared in isobutyl alcohol and has a P/V atom ratio of about 0.9–1.8:1. The vanadium is reduced to an average valence state of 3.9 to 4.6. The catalyst composition is said to have substantial intrinsic surface ara and a microcrystalline structure which result in advantageous activity in the catalyzed vapor phase oxidation of n-butane to maleic anhydride.

U.S. Pat. Nos. 4,062,873 and 4,064,070, issued to Harrison, disclose the preparation of an oxidation catalyst comprising oxides of vanadium, phosphorus, and silicon; and a process of preparing maleic anhydride by contacting the catalyst with hydrocarbon feed at a temperature of about 300° C. to 600° C. A catalyst precursor is prepared by co-precipitating a reduced vanadium oxide, silica or a silica precursor, and phosphoric acid. The precursor is calcined to form the silica-containing catalyst. The preferred vanadium oxidation state is between 3.5 to 4.6. Preferably, the silica is introduced in the form of an organic alkyl orthosilicate. The preferred P/V atom ratio is 0.9–3:1 and the preferred P/Si atom ratio is 20–1:1.

U.S. Pat. Nos. 4,132,670 and 4,187,235, issued to Katsumoto et al., disclose a method of preparing a vanadium/phosphorus oxide catalyst having an intrinsic surface area in excess of 10 square meters per gram. The catalyst is used in the oxidation of n-butane to maleic anhydride. Anhydrous alcohols of 1–10 carbon atoms and 1–3 hydroxyl groups are used to reduce the vanadium to a valence of 4.0 to 4.6. The catalyst has a V/P atom ratio of about 1:1.

U.S. Pat. Nos. 4,371,702 and 4,442,226, issued to Bither, disclose a vanadium/phosphorus oxide catalyst for the oxidation of n-butane to maleic anhydride and containing a promoter comprising silicon and at least one of indium, antimony and tantalum. The catalyst is prepared by initially contacting vanadium substantially of valence +4 with the promoter or promoter precursor in an aqueous or organic liquid medium. In an aqueous system, silica can be added to the vanadium as a colloidal silica sol. In an organic system, silica can be introduced as an alkyl orthosilicate. The patents subsequently disclose that a catalyst precursor is then formed by the addition of an appropriate phosphorus compound to give a composition which upon isolation and drying is blended with 1–3% of a die lubricant and pellet binder, such as graphite or Sterotex ®, a hydrogenated cottonseed oil commercially available from Capital City Products Company. The resulting combination is heated to generate the catalyst. The catalyst has a Si/V atom ratio of about 0.02–3.0:1.0, a (In+Sb+Ta)/V atom ratio of about 0.005–0.2:1.0 and a P/V atom ratio of about 0.9–1.3:1.0. The catalyst is contacted with n-butane at 300°–550° C. to form maleic anhydride.

U.S. Pat. No. 4,092,269, issued to Mount et al., discloses a method for preparing phosphorus/vanadium/oxygen catalysts useful in the manufacture of maleic anhydride. A pore modification agent is added to a catalyst precursor to provide a catalyst wherein the pore volume from pores having diameters between about 0.8 $\mu$m and about 10 $\mu$m is greater than 0.02 cc/g. In the preparation of a preferred catalyst, selected organic pore-modifying agents are incorporated into a catalyst precursor in an amount from about 2–15% by weight of precursor. The modifying agents are removed through combustion.

In any commercial process for the production of maleic anhydride, the product of n-butane conversion and selectivity to maleic anhydride should be maximized. In a process in which the off-gases following recovery of maleic anhydride are combusted, or in a recycle-type of operation, a high single pass yield of maleic anhydride is important.

SUMMARY OF THE INVENTION

The present invention provides an improved vanadium/phosphorus oxide catalyst for vapor phase oxidation of n-butane to maleic anhydride. The catalyst is prepared by the process comprising (1) contacting in an aqueous or organic liquid medium a vanadium species substantially of valence +4 with a sufficient amount of a phosphorus species, to form a catalyst precursor which will generate a P/V atom ratio in the range of from about 0.9:1.0 to about 1.3:1.0 in the catalyst; (2) blending the catalyst precursor with an organic pore modifying agent in an amount of from about 3 to about 5% by weight of the precursor and with fumed silica having a surface area of at least about 150 m²/g in an amount of from about 0.05 to about 0.20% by weight of the catalyst precursor; and (3) heating the resulting combination to generate the catalyst.

The present invention also provides an improved process for the oxidation of n-butane to maleic anhydride wherein n-butane is contacted with the specified catalyst for about 0.1 to about 15.0 seconds at a temperature of from about 300° to about 550° C. under pressure of from about 50 to about 2000 kPa.

DETAILED DESCRIPTION OF THE INVENTION

The present invention provides a process for preparing maleic anhydride by the vapor phase oxidation of n-butane and an improved oxidation catalyst for use in the process. The catalyst is a vanadium/phosphorus oxide catalyst which is prepared from a catalyst precursor containing fumed silica in an amount of from about 0.05 to about 0.20% by weight of catalyst precursor. More specifically, the invention provides:

1. An improved vanadium/phosphorus oxide catalyst for the oxidation of n-butane to maleic anhydride, said catalyst being prepared by blending a dried catalyst precursor with an organic pure modifying agent and a fumed silica in specified amounts. The resulting precursor blend, which may also contain selected promoters or promoter precursors, is shaped and subsequently heated under controlled thermal and atmospheric conditions. The resulting catalyst has a microstructure which leads to enhanced production of maleic anhydride; and 2. An improved catalytic process for the production of maleic anhydride comprising contacting n-butane with a vanadium/phosphorus oxide catalyst for about 0.1 to about 15 seconds at a temperature of from about 300° to about 550° C. under a pressure of from about 50 to about 2000 kPa, the improvement comprising using a vanadium/phosphorus oxide catalyst prepared by blending the catalyst's dried catalyst precursor with an organic pore-modifying agent and a fumed silica prior to heating.

It is to be understood that the above recitation of the invention does not include those process steps which are well-known and commonly used in the oxidation of n-butane to maleic anhydride and preparation of vanadium/phosphorus oxide catalysts. Following are additional details concerning the oxidation process and preparation of the catalyst of the invention.

In the present invention an oxide catalyst precursor is prepared by contacting a vanadium species substantially of valence +4 with a sufficient amount of a phosphorus species to form a catalyst having a P/V atom ratio of from about 0.9:1.0 to about 1.3:1.0. The catalyst precursor is isolated, dried, and blended with an organic pore-modifying agent in an amount of from about 3 to about 5% by weight of the precursor and about 0.05 to about 0.20% by weight of the precursor of fumed silica having a surface area of at least about 150 m$^2$/g. The resulting combination is heated to form a catalyst. Preferably, the catalyst contains a promoter of silicon and at least one of indium, antimony, and tantalum.

A vanadium compound wherein the vanadium is in the +5 oxidation state is initially reduced to a substantial degree to a tetravalent vanadium species by reactions in either an aqueous or organic liquid medium. This step is described in U.S. Pat. No. 4,442,226, the appropriate passages of which are incorporated herein by reference. Suitable pentavalent vanadium compous for use in preparing vanadium/phosphorus oxide catalyst precursors are known in the art. A partial list of suitable vanadium compounds include: vanadium oxides such as vanadium pentoxide, and the like; vanadium oxyhalides such as vanadyl trichloride, and vanadyl tribromide, and the like; vanadium containing acids such as metavanadic acid, and the like; vanadium salts such as ammonium metavanadate, and the like.

Reductants capable of reducing vanadium in the +5 oxidation state to a substantial degree to the +4 oxidation state are known in the art. In an aqueous medium, suitable reductants include soluble inorganic compounds, such as a concentrated halide acid like 38 volume percent hydrochloric acid; reduced acids of phosphorus like $H_3PO_3$; or soluble organic compounds like formaldehyde, ethylene glycol, or glycolic, oxalic, citric or tartaric acid. Preferably, the vanadium is reduced in an organic medium. In an organic medium, suitable reductants include at least one alcohol selected from the group consisting of n-propyl, isopropyl, n-butyl, isobutyl, and benzyl alcohol. The reduction can be conducted by slurrying the pentavalent vanadium compound in the liquid medium, followed by heating under reflux for the time necessary to bring about reduction.

Following substantial reduction of the +5 vanadium to the tetravalent species and the introduction of any desired promoter or promoter precursors, a catalyst precursor is formed by the addition of any commonly used phosphorus species in such amount that the P/V atom ratio in the ultimate catalyst is in the range of from about 0.9:1.0 to about 1.3:1.0. The sources of suitable phosphorus species are phosphorous compounds, such as phosphoric acid, which are known in the art. The resulting mixture is heated under reflux, cooled to ambient temperature and filtered to isolate the catalyst precursor. The precursor is dried in air at about 80° to about 200° C. to form a crystalline species having an X-ray diffraction pattern (Cu-K$\alpha$) with the following major peaks:

| d-Value, A | Intensity, I/I$_o$ |
| --- | --- |
| 5.70 | 100 |
| 4.52 | 43 |
| 3.67 | 29 |
| 3.29 | 37 |
| 3.11 | 17 |
| 2.94 | 54 |
| 2.79 | 14 |
| 2.66 | 16 |
| 1.90 | 11 |

An organic pore-modifying agent and fumed silica are incorporated into the catalyst precursor. These additives upon subsequent firing of the resultant blend generate a catalyst microstructure which leads to enhanced production of maleic anhydride. Suitable pore-modifying agents are known in the art. A partial list of suitable pore-modifying agents includes organic acids, polymeric materials, cellulosic materials, monosaccharides and polysaccharides, hydrogenated vegetable oils, waxes, and mixtures thereof. The preferred pore-modifying agent is a hydrogenated cottonseed oil which is commercially available from Capital City Products Company under the registered trademark Sterotex ®. The catalyst precursor contains about 3 to about 5% organic pore modifying agent by weight of precursor. The modifying agent also functions as a lubricant and binder when preparing shaped catalyst particles.

The vanadium/phosphorus oxide catalyst of the present invention contains fumed silica which is blended with the catalyst precursor in an amount from about 0.05 to about 0.20% by weight of isolated catalyst precursor. As used herein the expression "fumed silica" means a form of silica which is produced in a high-temperature, vapor-phase, process involving hydrolysis of a volatile silicon halide in a controlled flame of hydrogen and oxygen. Suitable fumed silica has a surface area of at least about 150 m²/g, preferably at least about 200 m²/g. The preferred fumed silica is commercially available from the Cabot Corporation under the registered trademark CAB-O-SIL ®. The silica functions as a moisture-controlling agent which improves powder flow characteristics. The catalyst precursor is blended with about 0.05 to about 0.20% fumed silica by weight of catalyst. Preferably, the catalyst precursor is blended with about 0.10 to about 0.15% fumed silica by weight of catalyst precursor, most preferably about 0.125%. The vanadium/phosphorus oxide composition is then shaped and subsequently heated under controlled thermal conditions in a controlled atmosphere to form the catalyst.

The catalyst precursor, following the blending with the pore-modifying agent and the fumed silica, is formed into a convenient catalyst shape, like pellets with a diameter of 3.2 or 4.8 mm (⅛ in or 3/16 in), for ultimate charge into a reactor. The pelleted catalyst precursor blend is fired in a controlled manner in order both to generate and to activate the catalyst species for use in the vapor phase oxidation of n-butane to maleic anhydride. In one embodiment, unactivated pellets are charged into a 2.54 cm (1 in) diameter quartz tube in a vertical furnace. The pellets are heated sequentially in a low flow of air (about 1 to 3 volumes/volume of catalyst/minute) at 375° to about 400° C. for 1 to 6 hours, and then in a more rapid gas flow (about 3 to 6 volumes/volume of catalyst/minute) of 1 to 1.5% n-butane in air (by volume) at 450° to about 490° C. for about 16 to 24 hours. In a preferred method which results in a more homogeneous product, the shaped catalyst precursor blend is initially fired in a continuous mode in a zoned belt furnace in an air atmosphere. The ends of the belt furnace are curtained with baffles and the heating units are set so as to maintain a reasonably smooth heating profile varying from about ambient temperature at the furnace ends to a maximum temperature of about 390°–395° C. in the center of the heated zone. The catalyst precursor blend is transported through the furnace at about 6.3 mm (¼ in) per minute which takes about 4 hours. Air diffuses in through the baffles to replace combustion products diffusing out through vertical vents located in the heated zone of the furnace. Catalyst weight loses (i.e., water and organics) generally run about 15% by weight and pellet densities drop about 5% or less during this pre-activation step. Activation of the catalyst is continued in a 2.54 cm (1 in) diameter vertical quartz reactor substantially as described previously by heating in a gas flow (about 3 volumes/volume of catalyst/minute) of about 1.5% n-butane in air (by volume) at a temperature of about 450° to about 470° C. for about 16 to 24 hours. The resulting activated catalyst is ready for use in the production of maleic anhydride.

The vanadium/phosphorus oxide catalyst of the present invention can contain a promoter which is a combination of selected materials. Any promoter capable of enhancing the catalytic oxidation of n-butane to maleic anhydride is suitable. A partial list of suitable promoters is disclosed in U.S. Pat. No. 4,442,226, the disclosure of which is incorporated herein by reference. Other promoters are known in the art. Preferably, the promoter is silicon and at least one of the variable valent elements selected from indium, antimony, and tantalum, as described in U.S. Pat. No. 4,442,226. Preferably, the preferred promoter or promoter precursor is combined with the substantially tetravalent vanadium compound in a specified order and chemical form following the reduction step, as described below. In a preferred embodiment, the catalyst has a Si/V atom ratio of about 0.02:1.0 to about 3.0:1.0, and a (In+Sb+Ta)/V atom ratio of about 0.005:1.0 to about 0.2:1.0, preferably about 0.02:1.0 to about 0.12:1.0. The P/V atom ratio is from about 0.9:1.0 to about 1.3:1.0.

In an aqueous system, silicon can be introduced in the form of a colloial silica sol. Preferred silica sols are commerically available from E. I. du Pont de Nemours and Company (Du Pont) under the registered trademark Ludox ®. In an organic system, the silicon can be added as an alkyl orthosilicate, like tetraethyl orthosilicate. When using the orthosilicate and $V_2O_5$, it is preferable to add at least 0.25 moles of orthosilicate per mole of $V_2O_5$ following the reduction of the pentavalent vanadium compound to the substantially +4 species.

Preferably, the indium, antimony, and/or tantalum is introduced into the reaction medium as soluble species. In an organic system, they can be added as a cation with an appropriate attendant anion, for example, an acetate, an alkoxide, or an anhydrous halide. The addition of indium, antimony, and/or tantalum compound can be carried out during the reduction of the pentavalent vanadium species. Preferably, the addition is subsequent to the initial charge of silicon compound in order to preclude and/or minimize hydrolysis thereof to a less desirable oxide species and prior to the addition of the appropriate phosphorus compound.

The oxidation of n-butane to maleic anhydride can be carried out using techniques known in the art in a variety of suitable reactors. The vapor phase oxidation can be conducted in a fixed-bed reactor by contacting the activated catalyst with a mixture of n-butane and oxygen, in appropriate concentrations, in the presence of one or more inert diluent gases. Air provides a suitable source of oxygen. Synthetic mixes of oxygen and such diluent gases as nitrogen, argon, helium, and water vapor, are also suitable. The explosive potential of a wide range of oxygen-butane mixtures combined with inert diluent gases must be recognized. The concentration of up to about 1.5 to 2.0% (by volume) butane in air represents the maximum safe range for the lower explosive limit. At an oxygen concentration reduced to about 10%, the restriction on butane no longer pertains. The vanadium/phosphorus oxide catalysts of the present invention show a sensitivity to oxygen partial pressure with respect to their catalytic activity. Preferably, the oxygen level in the feed is maximized within the limits of safe operability. In order to achieve maximum maleic anhydride production, the butane concentration is also maximized under the same regime.

Preferably, the oxidation of n-butane to maleic anhydride is conducted in a fixed-bed operation with a hydrocarbon concentration of about 1.5% in air (by volume) at a temperature from about 300° to 550° C., preferably, from about 350° to 450° C. Suitable operating pressures are about 50 to about 2,000 kPa (0.5 to 20 atm). Preferably, operating pressures are in the range 100 to about 700 kPa (1 to 7 atm), and most preferably in the range 200 to about 400 kPa (2 to 4 atm). Contact times, as expressed at standard temperature and pressure, are from about 0.1 to about 15.0 seconds, preferably from about 0.2 to about 6.0 seconds. The oxidation of n-butane to maleic anhydride with the catalyst of this invention can also be carried out in a fluidized-bed reactor. Due to the nature of the performance of a fluidized-bed reactor, oxidation of n-butane to maleic anhydride can be conducted at concentrations heretofore referred to as falling within the explosive region. Catalysts suitable for use in this type of system are capable of passing a sieve having 250 μm openings (No. 60 U.S. Standard Sieve) but incapable of passing a sieve having 45 μm openings (No. 325 U.S. Standard Sieve). Particles of this size can be generated by crushing and sieving pre-formed catalyst pellets whose preparation has been described previously.

Catalyst processing variables encompassing such items as drying, pelleting, and heating, all interact to influence catalyst microstructure which in turn affects ultimate catalyst performance. The loading level of fumed silica incorporated into the precursors of these catalysts is observed to be critical to this ultimate performance in the production of maleic anhydride and is found to be optimized at about 0.125% by weight. The importance of incorporating the specified amount of fumed silica into the precursors of the claimed catalysts is demonstrated by comparing the catalytic performance of catalysts prepared in the Examples of the invention with the performance of the Comparative Catalysts.

Catalyst productivity is a measure of the effectiveness of a quantity of catalyst in producing a desired product. This property, also known as Space Time Yield (STY), is defined herein as the number of grams of maleic anhydride (MAN) produced per kilogram of catalyst charged per hour of operating time. High yields of maleic anhydride and high gas flows over the catalyst maximize the productivity value. Very high gas flows at an operating pressure of 100 kPa (1 atm) will not necessarily generate high productivity, because the contact time of the feed stream over the catalyst bed may be of too short duration. The contact time can be increased for a given gas flow by increasing reaction pressure. If the mass and heat transfer properties of the catalyst are adequate, the yield of product will not be appreciably diminished due to adverse side reactions.

The present invention is further described by the following examples, wherein all parts and percentages are by weight, unless otherwise stated, and degrees are Celsius. The following two methods were used for testing catalytic activity of examples of the present invention and comparative catalysts:

TESTING METHOD I

Catalytic activity was determined in a 2.54 cm (1 in) diameter vertical quartz reactor heated in a three zone furnace. Activated catalyst pellets were charged to the reactor. A down-mode gas flow of 1.5% n-butane in air by volume was passed over the catalyst to produce maleic anhydride. The rate of gas flow was maintained at about 6 to 7 volumes/volume of catalyst/minute to give a contact time at standard temperature and pressure of about 3 to 3.5 seconds. The production of maleic anhydride was maintained for 24 hours at a maximum temperature of about 420°. The maleic anhydride produced was trapped in water. Yields were determined by titration. The single pass yield (SPY) of maleic anhydride produced was determined by dividing the moles of maleic anhydride produced by the moles of n-butane passed over the catalyst during the 24 hour collection period, times 100.

TESTING METHOD II

Catalytic activity was determined in a 2.54 cm (1 in) diameter stainless steel tube reactor with an internal volume of about 100 mL which was fitted at the lower end with a 150 mesh stainless steel screen for catalyst support. The reactor was charged with about 75 mL of activated catalyst pellets and the void space above the catalyst bed was filled with SiC, which was capable of passing a sieve having 2 μm openings (No. 10 U.S. Standard Sieve) but incapable of passing a sieve having 0.8 μm openings (No. 20 U.S. Standard Sieve), in order to suppress homogenous gas phase reactions. A gas mixture containing n-butane was passed over the catalyst in an up-mode. The reactor was fitted with a three-probe internal thermocouple to ascertain temperatures in the catalyst bed. External heating was carried out in a fluidized sand bath for good temperature control. A length of 3.2 mm (⅛ in) diameter stainless steel tubing wound into a tight coil and connected to the lower end of the vertical reactor, was also contained in the sand bath. The coiled tubing served as a feed pre-heater. The other end of the feed pre-heater was connected to a metered $N_2/O_2$/n-butane manifold. The reactor was connected so as to allow on-line transport of both feed and product streams at a temperature of about 200° from the feed manifold through the reactor and then to dual gas chromatographic (GC) facilities. Continuous heating served to pre-heat the feed and avoid deposition of maleic anhydride. A heated back-pressure valve was inserted in the exit line ahead of the GC train to allow operation of the reactor at a pressure from about 100 to 860 kPa (1 atm to 8.6 atm). The GC facilities determined the amounts of $N_2$, $O_2$, CO, $CO_2$, $H_2O$, n-butane, maleic anhydride, and compounds such as ethylene, furan, and methyl ethyl ketone in the product stream. The latter three appeared only in trace amounts in the oxidation process of this invention. With catalysts of this invention, CO was formed in larger amounts than $CO_2$, with the $CO/CO_2$ mole ratio usually in the range of from about 2.0:1.0 to about 1.3:1.0.

Yields were determined for four sets of operating conditions. Contact times ranged from about 2 to 5+ seconds. Operating pressures ranged from about 100 to 300 kPa (15–45 psia).

EXAMPLE 1

Preparation of Catalyst Containing 0.125% Fumed Silica

A catalyst precursor was prepared from vanadium pentoxide and phosphoric acid. 600 grams of commercial grade vanadium pentoxide were sieved through a sieve having 425 μm openings (No. 40 U.S. Standard Sieve) and ball milled for one hour in isobutyl alcohol. The resulting vanadium oxide plus 6 L of isobutyl alcohol and 0.6 L benzyl alcohol were charged into a 12 L, 4-neck flask equipped with stirrer, reflux condenser, dropping funnel, and heating mantle and heated under reflux for about 16 hours to bring about the substantial reduction of the vanadium to +4 valence. 192 grams of $Si(OEt)_4$ were added to the mixture and heating was continued under reflux for five hours. 23 grams of indium metal (corresponding to 3 atom percent In based upon V) treated in the following manner were added to the mixture and heating was continued under reflux for about two hours. The indium metal had been dissolved in a minimum amount of hydrochloric acid, taken to dryness on a steam bath, and redissolved in a minimum amount of glacial acetic acid (dried down twice from acetic acid). 540 grams of Si(OEt)$_4$ were added to the resulting mixture and heating under reflux was continued for about 16 hours to form a black slurry. 900 grams of 85% phosphoric acid were added to the slurry and heating under reflux was continued for about 24 hours. The resulting combination was cooled and the resultant turquoise blue slurry was filtered off, air dried, and then dried at a temperature of about 100° to form a catalyst precursor.

The catalyst precursor, which weighed 1200 g, was obtained in powder form. Scanning electron microscopy showed the physical form of the precursor to resemble tight "yarn-like" clusters of some 3 to 10 micron in size.

The catalyst precursor was blended with 36 grams of a pore-modifying agent, available commercially from Capital City Products Company under the registered trademark Sterotex ®. 200 grams of the resulting mixture were blended with 0.25 grams of a fumed silica, available commercially from the Cabot Corporation under the registered trademark Cab-O-Sil ® M-5, which provided a catalyst precursor blend which contained 0.125% fumed silica and 3% pore-modifying agent. The mixture of precursor, pore-modifying agent and fumed silica was shaped into 3.2 mm (⅛ in) pellets for thermal activation.

Pre-activation of the catalyst was conducted in a belt furnace. The pellets were heated at a maximum temperature of 390° in air to form sturdy, green-colored pellets having a density of about 1.5 g/mL and an average vanadium valence of about 4.4. The green-colored pellets showed a relatively low degree of X-ray crystallinity and were observed from their X-ray powder pattern to contain a mixture of tetra- and pentavalent vanadium/phosphorus oxide species, in accord with their observed average vanadium valence.

The final activation of the pellets was conducted in a 2.54 cm (1 in) diameter vertical quartz reactor. The reactor was heated in a three-zone furnace using a down-mode gas flow (3 volumes/volume of catalyst/minute) of 1.5% n-butane in air (by volume) at a maximum temperature of 459° for a period of 24 hours to form a catalyst. Catalytic activity was determined according to Testing Method I and the results are shown in Table 1. Activity was also determine according to Testing Method II and the results are shown in Table 2.

COMPARATIVE EXPERIMENT A

Preparation of Catalysts Containing No Fumed Silica

Catalyst precursor substantially as described in Example 1 was blended with 3% of the pore-modifying agent substantially as described in Example 1 and shaped into 3.2 mm (⅛ in) pellets. The pellets which contained no fumed silica were then pre-activated and activated similarly to the method described in Example 1 to form a catalyst. The catalytic activity of the catalyst was determined according to Testing Method I and II and the results are shown in Tables 1 and 2, respectively.

COMPARATIVE EXPERIMENT B

Preparation of Catalysts Containing 0.25% Fumed Silica

A combination of catalyst precursor and 3% pore-modifying agent substantially as described in Comparative Experiment A was blended with 0.25 percent of fumed silica substantially as described in Example 1. The resulting combination was shaped into 3.2 mm (⅛ in) pellets, pre-activated, and activated substantially according to the method described in Example 1 to form a catalyst. The catalytic activity of the catalyst was determined according to Testing Methods I and II and the results are shown in Tables 1 and 2, respectively.

EXAMPLES 2–4

Preparation of Catalyst Containing 0.125% Fumed Silica

Three catalysts were prepared using a procedure similar to the method described in Example 1, except only 19 grams of indium metal (corresponding to 2.5 atom percent In based upon V) prepared substantially in the manner described in Example 1, were incorporated into the catalytic precursor of Example 3. These catalysts were tested for catalytic activity according to Testing Method II and the results are shown in Table 2. The catalysts prepared in Examples 2 and 3 were tested according to Testing Method I and the results are shown in Table 1.

COMPARATIVE EXPERIMENTS C, E AND G

Preparation of Catalysts Containing No Fumed Silica

Using catalyst precursors similar to those prepared in Examples 2–4, three catalysts were prepared. Each catalyst precursor was blended with 3% of the pore-modifying agent substantially as described in Example 1 and shaped into 3.2 mm (⅛ in) pellets. The pellets which contained no fumed silica were then pre-activated and activated similarly to the method described in Example 1 to form catalysts. Portions of these catalysts were tested for catalytic activity according to Testing Method II and the results are shown in Table 2. Comparative Catalysts C and E were tested according to Testing Method I and the results are shown in Table 1.

COMPARATIVE EXPERIMENTS D, F AND H

Preparation of Catalysts Containing 0.25% Fumed Silica

Three combinations of catalyst precursor and 3% pore-modifying agent substantially as described in Comparative Experiments C, E and G were blended with 0.25 percent of fumed silica substantially as described in Example 1. The resulting combinations were shaped into 3.2 mm (⅛ in) pellets, preactivated, and activated substantially according to the method described in Example 1 to form catalysts. Portions of these catalysts were tested for catalytic activity according to Testing Method II and the results are shown in Table 2. Comparative Catalysts D and F were tested according to Testing Method I and the results are shown in Table 1.

The better performance of the catalysts within the scope of this invention is evident from the data presented in Tables 1 and 2.

TABLE 1

Oxidation of n-butane to Maleic Anhydride

CATALYST PERFORMANCE

| Comparative Catalyst | Example | Atom % In based on V | % Pore-modifying Agent Added to Precursor (%) | Fumed Silica Added to Precursor (%) | SPY | STY |
|---|---|---|---|---|---|---|
| A | — | 3 | 3 | 0 | 61 | 15 |
| — | 1 | 3 | 3 | 0.125 | 67 | 19 |
| B | — | 3 | 3 | 0.250 | 51 | 15 |
| C | — | 3 | 3 | 0 | 65 | 17 |
| — | 2 | 3 | 3 | 0.125 | 67 | 20 |
| D | — | 3 | 3 | 0.250 | 51 | 14 |
| E | — | 2.5 | 3 | 0 | 68 | 20 |
| — | 3 | 2.5 | 3 | 0.125 | 69 | 20 |
| F | — | 2.5 | 3 | 0.250 | 67 | 20 |

Notes:
SPY = SinglePass Yield - Maleic Anhydride Produced (moles)/n-butane (moles) passed over catalyst per 24 hour period of operation.
STY = Space Time Yield - Weight of Maleic Anhydride Produced (g)/Weight of catalyst charged (kg)/hour.

TABLE 2

Oxidation of n-Butane to Maleic Anhydride

| Comparative Catalyst | Example | Atom % In based on V | Pore-modifying Agent Added to Precursor (%) | Fumed Silica Added to Precursor (%) | CT~2 seconds 15 psia (100 Kpa) BT/MAN | SPY |
|---|---|---|---|---|---|---|
| A | — | 3 | 3 | 0 | 62/66 | 41 |
| — | 1 | 3 | 3 | 0.125 | 69/68 | 47 |
| B | — | 3 | 3 | 0.250 | 60/64 | 38 |
| C | — | 3 | 3 | 0 | 63/68 | 43 |
| — | 2 | 3 | 3 | 0.125 | 70/71 | 50 |
| D | — | 3 | 3 | 0.250 | 62/63 | 39 |
| E | — | 2.5 | 3 | 0 | 69/70 | 48 |
| — | 3 | 2.5 | 3 | 0.125 | 67/72 | 48 |
| F | — | 2.5 | 3 | 0.250 | 66/70 | 46 |
| G | — | 3 | 3 | 0 | 67/67 | 45 |
| — | 4 | 3 | 3 | 0.125 | 70/70 | 49 |
| H | — | 3 | 3 | 0.250 | 51/57 | 29 |

PERFORMANCE

| Comparative Catalyst | Example | CT~3-4 seconds 15 psia (100 Kpa) BT/MAN | SPY | 30 psia (200 Kpa) BT/MAN | SPY | CT~5+ seconds 45 psia (300 Kpa) BT/MAN | SPY |
|---|---|---|---|---|---|---|---|
| A | — | 70/69 | 48 | 64/63 | 40 | 65/56 | 36 |
| — | 1 | 80/71 | 57 | 70/69 | 48 | 84/61 | 51 |
| B | — | 74/65 | 48 | — | — | — | — |
| C | — | 80/70 | 56 | 71/66 | 47 | — | — |
| — | 2 | 79/75 | 59 | 70/73 | 51 | 75/71 | 53 |
| D | — | 72/66 | 48 | — | — | — | — |
| E | — | 78/72 | 56 | 65/75 | 49 | 71/71 | 50 |
| — | 3 | 83/72 | 60 | 73/72 | 53 | 76/67 | 51 |
| F | — | 81/71 | 58 | 70/71 | 50 | — | — |
| G | — | 78/70 | 55 | 67/68 | 46 | 72/64 | 46 |
| — | 4 | 87/70 | 61 | 78/68 | 53 | 80/67 | 54 |
| H | — | 68/57 | 39 | 68/45 | 31 | — | — |

Notes:
BT = % n-Butane Conversion
CT = Contact time
MAN = % Maleic Anhydride Selectivity
SPY = Maleic Anhydride Yield MAN (moles)/n-BT (moles)/unit time

I claim:

1. An improved vanadium/phosphorus oxide catalyst for vapor phase oxidation of n-butane to maleic anhydride;
   said catalyst being prepared by the process comprising:
   (a) contacting in an aqueous or organic liquid medium a vanadium species substantially of valence +4 with a sufficient amount of a phosphorus species, to form a catalyst precursor which will generate a P/V atom ratio in the range of from about 0.9:1.0 to about 1.3:1.0 in the catalyst;
   (b) blending the catalyst precursor with an organic pore modifying agent in an amount of from about 3 to about 5% by weight of the precursor and with fumed silica having a surface area of at least about 150 m$^2$/g in an amount of from about 0.05 to about 0.20% by weight of the catalyst precursor; and
   (c) heating the resulting combination to generate the catalyst.

2. A catalyst according to claim 1, wherein fumed silica is in an amount of from about 0.10 to about 0.15% by weight of the catalyst precursor.

3. A catalyst according to claim 2, wherein fumed silica is in an amount of about 0.125% by weight of the catalyst precursor.

4. A catalyst according to claim 3, wherein the organic pore modifying agent is hydrogenated cottonseed oil.

5. A catalyst according to claim 3, wherein the fumed silica has a surface area of at least about 200 m²/g.

6. A catalyst according to claim 5, wherein said vanadium species in step (a) is contacted with a sufficient amount of a promoter comprising silicon and at least one of indium, antimony, and tantalum to form a catalyst precursor which will generate a Si/V atom ratio from about 0.02::1.0 to about 3.0:1.0 and an (In+Sb+Ta)/V atom ratio of from about 0.005:1.0 to about 0.2:1.0 in the catalyst.

7. A catalyst according to claim 6, wherein the (In+Sb+Ta)/V atom ratio is from about 0.02:1.0 to about 0.12:1.0.

8. A method for preparing a vanadium/ phosphorus oxide catalyst for vapor phase oxidation of n-butane to maleic anhydride, comprising the steps of:
   (a) contacting in an aqueous or organic liquid medium a vanadium species substantially of valence +4 with a sufficient amount of a phosphorus species, to form a catalyst percursor which will generate a P/V atom ratio in the range of from about 0.9:1.0 to about 1.3:1.0 in the catalyst;
   (b) blending the catalyst precursor with an organic pore modifying agent in an amount of from about 3 to about 5% by weight of the precursor and with fumed silica having a surface area of at least about 150 m²/g in an amount of from about 0.05 to about 0.20% by weight of the catalyst precursor; and
   (c) heating the resulting combination to generate the catalyst.

9. A method as defined in claim 8, wherein fumed silica is in an amount of from about 0.10 to about 0.15% by weight of the catalyst precursor.

10. A method as defined in claim 9, wherein fumed silica is in an amount of about 0.125% by weight of the catalyst precursor.

11. A method as defined in claim 10, wherein the organic pore modifying agent is hydrogenated cottonseed oil.

12. A method as defined in claim 10, wherein the fumed silica has a surface area of at least about 200 m²/g.

13. A method as defined in claim 12, wherein said vanadium species in step (a) is contacted with a sufficient amount of a promoter comprising silicon and at least one of indium, antimony, and tantalum to form a catalyst precursor which will generate a Si/V atom ratio of about 0.02:1.0 to about 3.0:1.0 and an (In+Sb+Ta)/V atom ratio of from about 0.005:1.0 to about 0.2:1.0 in the catalyst.

14. A method as defined in claim 13, wherein the (In+Sb+Ta)/V atom ratio is from about 0.02:1.0 to about 0.12:1.0.

* * * * *